United States Patent [19]

Belanger et al.

[11] Patent Number: 4,835,268

[45] Date of Patent: May 30, 1989

[54] LUMINESCENT CYCLIC HYDRAZIDES FOR ANALYTICAL ASSAYS

[75] Inventors: Alain Belanger, Cap-Rouge; Paul Brassard, Ste-Foy, both of Canada

[73] Assignee: Universite Laval, Quebec, Canada

[21] Appl. No.: 46,869

[22] Filed: May 7, 1987

[30] Foreign Application Priority Data

May 8, 1986 [CA] Canada ................................. 508758

[51] Int. Cl.⁴ ............................................. C07D 237/32
[52] U.S. Cl. ....................................... 540/599; 544/237; 548/406; 548/466; 548/525; 549/214; 549/243; 252/700
[58] Field of Search .................. 252/700; 540/599; 544/237; 548/406, 466, 525; 549/214, 243

[56] References Cited

U.S. PATENT DOCUMENTS

| | | |
|---|---|---|
| 4,207,112 | 6/1980 | Ikenoue et al. ..................... 430/566 |
| 4,297,273 | 10/1981 | Buckler et al. ..................... 436/800 |
| 4,478,817 | 10/1984 | Campbell et al. ................... 436/547 |

FOREIGN PATENT DOCUMENTS

| | | |
|---|---|---|
| 0087959 | 9/1983 | European Pat. Off. . |
| 0116454 | 8/1984 | European Pat. Off. . |

OTHER PUBLICATIONS

F. Gorus and E. Schram, Clin. Chem., 25, 512 (1979).
T. P. Whitehead et al., Clin. Chem., 25, 1531 (1979).
M. Pazzagli et al., Clin. Chim. Acta, 115, 287 (1981).
F. Kohen et al., J. Steroid Biochem., 19, 413 (1983).
J. De Boever et al., Clin. Chem., 30, 1637 (1984).
P. J. Cheng et al., J. Immunol. Methods, 48, 159 (1982).
G. J. Barnard et al., Clin. Chem., 30, 538 (1984).
H. R. Schroeder et al., J. Immunol. Methods, 25, 275 (1979).
H. D. K. Drew and F. H. Pearman, J. Chem. Soc., 26 (1937).
H. D. K. Drew and F. H. Pearman, J. Chem. Soc., 586 (1937).
H. D. K. Drew and R. F. Garwood, J. Chem. Soc., 1841 (1937).
R. B. Brundrett and E. H. White, J. Amer. Chem. Soc., 96, 7497 (1974).
H. R. Schroeder and F. M. Yeager, Anal. Chem., 50, 1114 (1978).
H. R. Schroeder et al., Methods in Enzymology, 57, 424 (1978).
T. Proll and W. Walter, Chem. Ber, 116, 1564 (1983).

*Primary Examiner*—Robert J. Warden
*Assistant Examiner*—Robert Benson
*Attorney, Agent, or Firm*—Swabey, Mitchell, Houle, Marcoux & Sher

[57] ABSTRACT

Disclosed herein are derivatives of 5-(lower alkyl)-7-amino-2,3-dihydro-1,4-phthalazinedione having substituents on the amino group. The derivatives have luminescent properties which render them useful as analytical tools in clinical chemistry. Adaptation of the derivatives for luminescent immunoassay provides valuable reagents and assays with outstanding sensitivity.

15 Claims, No Drawings

LUMINESCENT CYCLIC HYDRAZIDES FOR ANALYTICAL ASSAYS

BACKGROUND OF THE INVENTION

This invention relates to luminescent substances and their use in clinical chemistry. More specifically, the invention relates to new luminescent cyclic hydrazides useful as analytical tools in clinical chemistry, to a process and intermediates for preparing the cyclic hydrazides, to cyclic hydrazide complexes or conjugates for use as reagents for luminescent immunoassay (LIA's), and to methods and kits for performing the assays.

Luminescent compounds have been used extensively in clinical chemistry; see reviews by F. Gorus and E. Schram, Clin. Chem. 25, 512 (1979) and T. P. Whitehead et al., Clin. Chem., 25, 1531 (1979). They have been demonstrated to be effective analytical tools in general, and a particular area of interest is their potential use as labels or tags for immunoassays. Presently, the most commonly used immunoassay is the radioimmunoassay (RIA). However, the RIA suffers from disadvantages inherent with the use of radioisotopes, such as radiation hazard and the relatively short half-life of certain isotopes. Hence, as expressed in the noted two reviews, interest in the development of nonisotopic labels has been increasing and in particular more attention is being focused on the possible replacement of RIA by LIA.

Indeed, LIA procedures have recently been reported for steroids, M. Pazzagli et al., Clin. Chem. Acta, 115, 287 (1981), F. Kohen et al., J. Steroid Biochem., 19, 413 (1983) and J. De Boever et al., Clin. Chem., 30, 1637 (1984); for proteins, P. J. Cheng et al., J. Immunol. Methods, 48, 159 (1982) and G. J. Barnard et al., Clin. Chem., 30, 538 (1984); and for other biological compounds, H. R. Schroeder et al., J. Immunol. Methods, 25, 275 (1979). These reports demonstrated the practicality of LIA procedures. However, the trend toward increasingly sophisticated techniques and the demand for detecting even more minute traces of analytes has created a need for more sensitive assays.

Two factors play a major role in the sensitivity of an immunoassay: the affinity of antibodies for the tracer and the specific activity of the latter. In LIA, the specific activity of the tracer is light emission and the quantum yield of the light is usually the most important parameter affecting the sensitivity of the assay.

Thus, the search for improved luminescent tags has rekindled the interest in cyclic hydrazides exhibiting chemiluminescence. The first cyclic hydrazide reported to have this property was luminol(5-amino-2,3-dihydro-1,4-phthalazinedione), H. O. Albrecht, Z. Phys. Chem., 136, 321 (1928). Since that report, a number of investigations have been directed to determining the factors that influence light production in luminol and related cyclic hydrazides. (Hereinafter, the term 'cyclic hydrazide' will be used to designate compounds having a 2,3-dihydro-1,4-phthalazinedione ring system.) Several of these factors were identified very early by Drew and his coworkers as substituent effects, see H. D. K. Drew and F. H. Pearman, J. Chem. Soc., 26 and 586 (1937) and H. D. K. Drew and R. F. Garwood, J. Chem. Soc., 1841 (1937). Subsequent investigations have confirmed and expanded Drew's observations, see R. B. Brundrett and E. H. White, J. Amer. Chem. Soc., 96, 7497 (1974), and H. R. Schroeder and F. M. Yeager, Anal. Chem., 50, 1114 (1978).

In summary, the previous investigations have shown that in cyclic hydrazides the unimpeded resonance of electron-donating groups with the phenyl portion of the ring system generally exerts a favorable influence on the luminescent process as does mild steric interaction of certain substituents with adjacent carboxyls at C-1 and C-4, and that substitution of the heterocyclic moiety completely inhibits the process.

So far, the search for cyclic hydrazide luminescent labels has been directed mainly to derivatives of isoluminol(6-amino-2,3-dihydro-1,4-phthalazinedione) rather than luminol. Ligandchemiluminescent labeled conjugates derived from isoluminol are more efficient than those derived from luminol, apparently because of the relatively less steric hindrance exerted on the C-4 carbonyl of the isoluminol ring system. H. R. Schroeder et al., Methods in Enzymology, 57, 424 (1978) prepared several luminescent compounds and found that 6-[N-(4-amino-butyl)-N-ethylamino]-2,3-dihydro-1,4-phthalazinedione (ABEI) functioned as an efficient chemiluminescent label. The use of this derivative in LIA has resulted in a procedure with a sensitivity comparable to that of RIA: see Pazzagli et al., Kohen et al., and De Boever et al., supra.

Notwithstanding the advances made to date, there still remains a niche in clinical chemistry for more efficient luminescent compounds and, in particular, a need for markers that would give LIA systems of greater sensitivity.

Accordingly, the present application discloses the preparation of new cyclic hydrazides with improved light emission characteristics, useful as analytical tools in clinical chemistry. Moreover, adaptation of these compounds for LIA provides valuable reagents and assays with outstanding sensitivity.

The cyclic hydrazides are isoluminol derivatives. They are distinguished from previously known isoluminol derivatives by having an alkyl substituent in a meta position to the amino substituent on the phenyl portion of the ring system; notwithstanding the existence of broad generic disclosures of a myriad of compounds ranging in the millions, see S. Ikenoue et al., U.S. Pat. No. 4,207,112, June 10, 1980; T. J. N. Carter et al., European Patent Application No. 83301030.9, published Sept. 7, 1983; T. P. Whitehead et al., European Patent Application No. 84300725.3, published Aug. 22, 1984; and A. K. Campbell et al., U.S. Pat. No. 4,478,817, Oct. 23, 1984.

SUMMARY OF THE INVENTION

The new cyclic hydrazides disclosed herein are represented by formula 1:

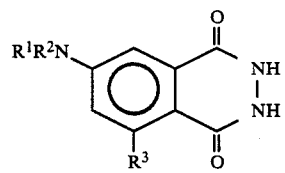

wherein $R^1$ and $R^2$ together with the nitrogen to which they are attached represent a 1-pyrrolidinyl, 1-piperidinyl or 1-azepinyl; or $R^1$ is lower alkyl and $R^2$ is lower alkyl or substituted alkyl of the formula $CHR^4CHR^5$—ALK—X wherein each of $R^4$ and $R^5$ is hydrogen or methyl, ALK is a divalent alkylene having 1 or 2 carbon atoms, or 3 to 5 carbon atoms in a straight chain, with optional substitution of a methyl on one or more of the carbon atoms, and X is halo, hydroxy, carboxy or amino; and $R^3$ is lower alkyl.

A preferred group of cyclic hydrazides is represented by formula 1 wherein $R^1$ and $R^2$ together with the nitrogen to which they are attached represent a 1-pyrrolidinyl or 1-piperidinyl, and $R^3$ is methyl, ethyl, propyl or butyl.

Another preferred group of cyclic hydrazides is represented by formula 1 wherein each of $R^1$, $R^2$ and $R^3$ is methyl, ethyl, propyl or butyl.

Still another preferred group is represented by formula 1 wherein each of $R^1$ and $R^3$ is lower alkyl and $R^2$ is $CH_2CH_2$—ALK—X wherein ALK is a divalent alkylene having 1 or 2 carbon atoms, or 3 to 6 carbon atoms in a straight chain, and X is hydroxy, carboxy or amino.

A more preferred group is represented by formula 1 wherein each of $R^1$ and $R^3$ is methyl or ethyl and $R^2$ is $(CH_2)_mX$ wherein m is an integer from 3 to 8 and X is hydroxy, carboxy or amino.

A process for preparing the cyclic hydrazides of formula 1 is disclosed hereinafter.

The cyclic hydrazides are extremely effective luminescent compounds. For this reason they are useful as analytical tools in clinical chemistry.

A specific use for the cyclic hydrazides of formula 1 wherein $R^2$ is a substituted alkyl as defined hereinabove entails their application as labels for LIA's. Accordingly, luminescent reagents and immunoassay methods are provided herein for detecting or quantifying extremely small amounts of a wide range of biological analytes originating in body fluids. (Hereinafter; "biological analyte" will be referred to as a ligand or as a unlabeled ligand.)

One kind of LIA that benefits from having the last named cyclic hydrazides as labels is the immunoassay based on the competitive immunological reaction wherein the antigenic ligand to be assayed competes with its labeled counterpart (in the present case, a specimen of the ligand chemically linked to the cyclic hydrazide) for sites on an antibody of the ligand.

Another kind of LIA that benefits is known as the "two site" or "sandwich" immunometric assay. This assay is based on the ability of polyvalent antigens, such as protein ligands or medium to large peptide ligands, to form a ternary complex of the ligand itself, a unlabeled antibody bound to a solid-phase immunoabsorbent and a second antibody bearing a label as a result of it being chemically linked to the luminescent compound (in the present case, the last mentioned cyclic hydrazide of formula 1).

A particular reagent for the competition immunoassay is the conjugate formed by chemically linking a luminescent cyclic hydrazide of formula 1 wherein $R^2$ is a substituted alkyl as defined herein with a specie of the ligand to be assayed.

A particular agent for the immunometric assay is the conjugate formed by chemically linking a cyclic hydrazide of formula 1 wherein $R^2$ is a substituted alkyl as defined herein with an antibody to the ligand to be assayed.

Kits can be provided where the reagents are included in premeasured amounts so that they may be used directly or diluted to give assay reagent solutions having concentrations which substantially optimize the sensitivity and performance of the assay.

DETAILED DESCRIPTION OF THE INVENTION AND PREFERRED EMBODIMENTS

Definitions:

The term "lower alkyl" as used herein means straight chain alkyl radicals containing one to four carbon atoms and branched chain alkyl radicals containing up to four carbon atoms and includes, methyl, ethyl, propyl, 1-methylethyl, butyl, 2-methylpropyl and 1,1-dimethylethyl.

The term "ALK" as used herein means a divalent alkyl radical derived from a straight or branched chain aliphatic hydrocarbon by removal of two hydrogen atoms. The hydrocarbon contains 1 or 2 carbon atoms, or 3 to 6 carbon atoms in a straight chain, with optional substitution of a methyl on one or more of the carbon atoms, and includes, for example:

$-CH_2-$, $-CH_2CH_2-$, $-CH(CH_3)-$, $-(CH_2)_3-$, $-(CH_2)_4-$, $-CH_2CH(CH_3)CH_2-$ and $-CH_2-$, $-CH_2CH_2-$, $-CH(CH_3)-$, $-(CH_2)_3-$, $-(CH_2)_4-$, $-CH_2CH(CH_3)CH_2-$ and $-(CH_2)_2CHCH_2CH_3$.
           |

The term 'halo' as used herein means the halo radical selected from bromo, chloro and iodo.

The term 'silylating agent' means a tetrasubstituted silane of the type having a chloro, bromo or iodo atom as one substituent with the remaining substituents being alkyl or phenyl, the agent being capable of trapping an enolate ion in the form of a silyl enol ether. Examples of silylating agents include trimethylsilyl chloride, dimethylisopropylsilyl chloride, triphenylsilyl chloride and tert-butyldimethylsilyl chloride.

The term 'trisubstituted silyl' means the radical derived by removal of the halogen from the aforementioned silylating agent.

The term 'ligand' as used herein means the analyte, or substance of biological origin, whose presence or amount thereof in a liquid medium is to be determined or assayed as the case may be.

The term 'binding analog' in reference to a ligand is a substance which has the same immunological properties as the ligand.

The term 'antibody' as used herein means a substance which has a specific binding affinity for the ligand, or its binding analog, to the exclusion of other substances. The term encompasses monoclonal antibodies and polyclonal antibodies.

The term 'label' as used herein is a compound such as the present cyclic hydrazides, which in combination with other compounds produces a molecule in an electronically excited state, which in turn can decay to a lower energy state by the emission of light (i.e. luminescence or chemiluminescence).

The term 'activator' means a compound, or combination of compounds, which will react with the label to effect the chemiluminescent reaction inherent in the label.

The term 'peroxide producing compound' as used herein means a compound which upon reaction produces a peroxide group, e.g. sodium peroxide, and includes any peroxidase enzyme, e.g. microperoxidase, which elicits the luminescent reaction of luminol and like compounds.

Preparation of Cyclic Hydrazides:

The isoluminol derivatives of formula 1 can be prepared by a process illustrated by the following flow diagram wherein $R^1$ and $R^2$ of the radical $R^1R^2N$ are as defined hereinabove; $R^3$ is lower alkyl; $R^6$ is a trisubstituted silyl; $R^7$ is methyl or ethyl; and $R^1R^8N$ is a tertiary amino radical wherein $R^1$ and $R^8$ together with the nitrogen to which they are attached represent a 1-pyrrolidinyl, 1-piperidinyl or 1-azepinyl or $R^1$ is lower alkyl and $R^8$ is lower alkyl or a substituted lower alkyl of the formula $CHR^4CHR^5$—ALK—Y wherein $R^4$, $R^5$ and ALK are as defined herein for $R^2$ and Y is halo, O-(trisubstituted silyl), COO-(trisubstituted silyl) or NH-(trisubstituted silyl).

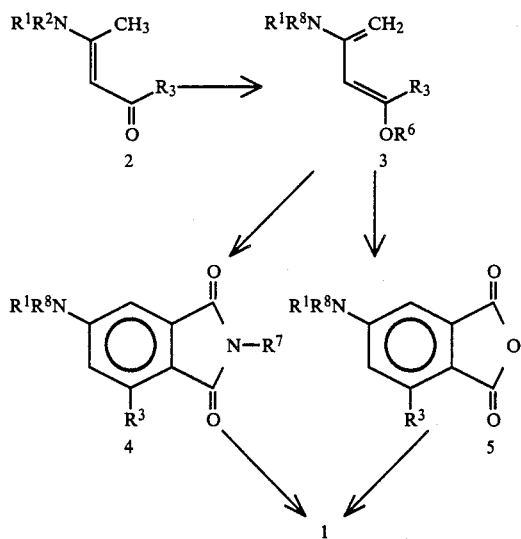

The starting materials, i.e. the enaminones of formula 2, are prepared by known methods. A convenient process is the one described by N. J. Leonard and J. A. Adamcik, J. Amer. Chem. Soc., 81, 595 (1959), involving the reaction of the appropriate amine (or protected amines if required) and a β-chloro-α,β-unsaturated ketone of formula $CH_3$—$CCl$=$CHCOR^3$ wherein $R^3$ is lower alkyl. The latter ketone, in turn, is prepared by known methods, see R. D. Clark and C. H. Heathcock, Synthesis, 47 (1974), from its corresponding β-diketone of formula $CH_3COCH_2COR^3$ in which $R^3$ is as defined herein.

The aforementioned amines are commercially available, e.g. benzylamine, 1,4-butanediamine, 3-chloropropylamine or 6-aminohexanoic acid, or can be prepared by known methods.

Referring to the flow diagram, reaction of the enaminone of formula 2 with a silylating agent, for instance trimethylsilyl chloride or preferably tert-butyldimethylsilyl chloride, affords the diene of formula 3.

The silylation of 'tertiary' type, N,N-disubstituted enaminone, of formula 2 is noteworthy. Recently, T. Proll and W. Walter, Chem. Ber., 116, 1564 (1983), reported that the silylation of enaminones wihout a substituent on the nitrogen occurs under facile conditions to give N-substituted products, and that the silylation of the 'secondary' type N-monosubstituted enaminones, under more stringent conditions, occurs with exclusive silylation at the oxygen atom. However, the silylation of N,N-disubstituted enaminones has remained unknown until now. In the instant situation, it was found necessary to use a strong base, for example, lithium diisopropylamide, in aprotic media, for instance a medium containing tetramethylethylenediamine, to effect the regiospecific (and probably kinetic) removal of the hydrogen in the γ-position of the N,N-disubstituted enaminone. The resultant enolate was then trapped as the enol silyl ether (i.e., the compound of formula 3) by reaction with the silylating agent.

It should also be noted that in the case where $R^2$ is a substituted alkyl bearing a hydroxy, carboxy or amino group, silylation of such substituents will compete with the silylation of the aforementioned enolate. Appropriate protection can be afforded for these groups (see E. Schröder and K. L. Lübke, "The Peptides", Vol. 1, Academic Press, New York, N.Y., 1965, pp. 3-128); however, for practical reasons, the silylation can be performed in this instance with an excess of silylating agent so that both the enolate and the competing substituent become silylated. The silyl group thereafter remains on the substituted alkyl portion throughout the remainder of the process and is removed at the end.

The dienes of formula 3, being relatively unstable, are used immediately for the next step.

Accordingly, the diene is reacted with a dienophile whereby all the substituents for the final product are introduced onto an intermediate bicyclic structure. It is essentially this step that eventually leads to the meta relationship of the amino substituent and the alkyl substituent on the phenyl moiety of the cyclic hydrazide, a relationship which is not possible by prior art routes to isomeric compounds wherein 3-alkylphthalic anhydrides are nitrated at positions 4 and 6 leading to an ortho or para relation of the corresponding substituents, see R. B. Brundrett and E. H. White, supra.

More specifically, the diene of formula 3 is reacted with a N-lower alkyl maleimide, for instance the dienophiles N-ethylmaleimide or preferably, N-methylmaleimide, under the conditions of the Diels-Alder reaction to give the corresponding cycloaddition product which is then aromatized by contact with a dehydrogenating catalyst, for example palladium, platinum, or Raney nickel, to give the corresponding phthalimide of formula 4. The addition of the dienophile is best performed at 5° to 10° C. in an inert solvent, e.g. toluene or benzene, using approximately equal molar amounts of the diene and dienophile.

Alternatively, the diene-dienophile condensation comprises the reaction of the diene of formula 3 with a halomaleic anhydride, preferably bromomaleic anhydride or chloromaleic anhydride, to afford the corresponding cycloaddition product which in turn is aromatized readily by heat or by contact with a surface-active agent capable of aromatizing cycloaddition products of dienes and halomaleic anhydride to give the phthalic anhydride of formula 5.

Suitable conditions for this cycloaddition are the same as those noted for the previous diene-dienophile addition. Aromatization of the cycloaddition product can be effected best by contacting the adduct with the surface-active agent silica gel. In fact, the desired phthalic anhydride 5 can be obtained conveniently in a pure state by placing the precursor cycloaddition product directly on a column of silica gel and eluting the column.

Thereafter, the reaction of hydrazine with the N-(lower alkyl)phthalimide of formula 4, or with the phthalic anhydride of formula 5, and if required removal of residual protecting groups or silyl groups, affords the cyclic hydrazide of formula 1. The reaction with hydrazine is accomplished most readily by heating the phthalimide or phthalic anhydride with an excess of hydrazine hydrate at 30° to about 120° C. from one to four hours. Optionally, acetic acid or water may be used as a medium for the reaction.

Finally, cleavage of residual protection groups or silyl groups, if present, is effected by deprotecting agents and desilylating agents, respectively, according to known methods; see, for instance, Schröder and Lübke, supra, and W. P. Weber, "Silicon Reagents for Organic Chemistry", Springer-Verlag: Berlin, 1983, pp. 206-272. A convenient method for the removal or residual silyl groups is the method of E. J. Corey and A. Venkateswarlu, J. Amer. Chem. Soc., 94, 6190 (1972) using tetra-n-butylammonium fluoride.

Luminescence and Luminescent Labels:

The luminescent properties of the cyclic hydrazides of formula 1 can be demonstrated according to known methods. (See, for example, the review by Gorus and Schram, supra.) As disclosed hereinafter in more detail, comparative data obtained from measurements of the luminescence of the present cyclic hydrazines and of the currently most interesting known cyclic hydrazides show that the present compounds have a substantially higher intensity of light emission than exhibited by the known chemiluminescent compounds.

This extremely efficient luminescent property for the present compounds renders them useful as valuable analytical tools for clinical chemistry, see the review by Whitehead et al., supra.

In particular, the intensity of their luminescent reactions renders them as suitable constituents for luminescent compositions for reaction with an activator to produce chemiluminescent light. The compositions can be employed to provide sensitive luminescent assays for adenosine triphosphate, NADH, NADPH and hydrogen peroxide, when these substances are produced in enzymatic systems. For example, the described assays by G. Wettermark et al., Coll. Mol. Biol., 22, 329 (1977), in this connection, are rendered luminescent compounds for the chemiluminescent process.

A particularly noteworthy use of the cyclic hydrazides of formula 1 in which $R^2$ is a substituted alkyl as defined herein is their use as labels in the preparation of reagents for LIA. Accordingly, the compounds can be coupled with ligands or antibodies to the ligands to afford an immunologically active, binding partner-luminescent substance conjugate for LIA; namely a labeled ligand or a labeled antibody to the ligand. Examples of ligands that can be used in this connection are proteins, peptides, hormones, haptens, steroids, nucleic acids and chemically synthesized substances. Examples of antibodies are those of the IgG, IgE, IgM and IgA classes, for example heptatitis B antibodies, which in a particular case can also be the ligand. Among the more important protein ligands there can be mentioned insulin, chorionic gonadotropin, carcinoembryonic antigen, myoglobin, hemoglobin, luinizing hormone, follicle simulating hormone, prolactin, human growth hormone, thyroid stimulating hormone, human placental lactogen and thyroxine; as well as enzymes, for instance, alkaline phosphatase and lactic dehydrogenase. Representative of peptide ligands are oxytocin, vasopressin, gastrin, atrial natriuretic factor, gastrin, and glucagon. Representative of steroids are progesterone, estriol and testosterone.

Various procedures for directly attaching or bridging the luminescent label to the ligand or to the antibody are well know; for instance, see T. J. M. Carter, et al., European patent applications No. 83301030.9, published Oct. 7, 1983.

In this instance, it is to be understood that the ligand moeity can be the specifically bindable ligand, or an analog therof having the same immunological specificity of the ligand, and that labeled reagents can be formed by direct condensation (usually forming an amide bond) or by bridging with an bifunctional coupling agent (e.g. glutaraldehyde) between the cyclic hydrazide and the ligand, ligand analog or antibody.

The Assay Method:

Several tyes of LIA's are known. The types are usually distinguished as being homogeneous or heterogeneous, involving either direct or competive binding, the heterogeneous types can, also involve solid phase techniques. The various types have been described, for instance, by R. C. Boguslaski et al., U.S. Pat. No. 4,363,759, Dec. 14, 1982, by G. S. David and H. E. Greene, U.S. Pat. No. 4,376,110, Mar. 8, 1983, by Whitehead et al., supra, and by Carter et al., supra.

When the quantifying or detecting step in one of these procedures involves a cyclic hydrazide marker or tracer, the use of the present cyclic hydrazides results in an improved and more sensitive assay.

In this regard, the present labeled ligands are particularly choice reagents for the heterogeneous, competitive binding type of assay. The competitive binding assay for detecting or quantifying a ligand in a medium comprises reacting a unknown amount of the ligand to be assayed with a known amount the corresponding labeled ligand and a known, but limited, amount of the antibody specific for the ligand under conditions that permit the competitive reaction between the labeled and unlabeled ligands for the receptor sites on the antibody to come to equilibrium; physically separating the bound ligand and bound labeled ligand from the corresponding unbound ligands; and activating the label in either fraction to yield a quantum of light. The quantum of light is a measure of the amount, or an indication of the presence of, the ligand in the amount of the ligand. Also the amount of labeled ligand that becomes bound to the antibody varies inversely to the unknown present. A useful and practical variation of the competitive heterogeneous binding assay using the present labeled ligand involves solid phase technology wherein the antibody is linked to a solid-phase immunoabosrbent, e.g. a plastic microplate, tube or sphere.

In the foregoing competitive binding assay, the three reaction components can be brought together either sequentially (the order not being critical) or simultaneously. Moreover, it will be apparent to those skilled in the art that in as much as the two ligands share an immunological relationship with the antibody, namely the ligand and the labeled ligand each represent a member of an immunological pair in which the other member is the antibody, the roles of the binding relationship can be interchanged.

An alternate embodiment, therefore, would be the situation wherein a labeled antibody and unlabeled antibody are competing for a ligand.

Labeled antibodies also play an important role in the two-site immunometric assay for determining the amount or presence in a liquid medium such as a serum sample, of an antigenic protein ligand or an antigenic large peptide ligand. In a typical application of this assay, the ligand, a given quantity of a unlabeled antibody bound to a solid-phase immunoabsorbent, and a given quantity of second antibody labeled with a compound of formula 1 wherein $R^2$ is as defined herein, are brought into contact, either in random sequence or simultaneously, under conditions which allow the attainment of an equilibrium state for the reactants. In this manner a solid ternary complex of the antigenic substance and the two antibodies is formed. Subsequent separation of the solid complex from the liquid phase, and activation of the luminescent label in either the solid or liquid fraction gives a quantum of light which is a measure of the amount, or an indication of the presence, of the ligand in the liquid medium.

Still another alternate embodiment would be one wherein the antibody for the above noted assays is a monoclonal antibody.

Particular antibodies can be purchased commercially or they can be prepared by known immunological techniques.

The Luminescent Reaction:

Light emission from the luminescet reaction is dependant on several factors. The efficiency of the emission depends on reagent concentration, temperature, pH, choice of activator, mixing sped and the manner of light measurement. Normally, optimum results are obtained for the luminescent reaction by conducting the same in an aqueous medium in the presence of a strong base, preferably sodium hydroxide or potassium hydroxide, a buffer and an activator. The temperature usualy ranges from 10° to 50° C. and the pH of the reaction medium ranges from 6 to 14, most often at 10 to 14. Suitable buffering substances include carbonates, borates, phosphates, (trishydroxymethyl)aminomethane and acetates. The particular buffer employed is not critical, but in inivdual assays, one buffer may be preferred over another.

The concentration of the base and activator are kept constant as a rule.

The concentration of the binding partnerluminescent substance conjugate may vary widely and will depend upon a variety of factors such as the sensitivity of the detection system, and the number of chemiluminescent molecules attached to a specific antigenic ligand or antibody molecule. Furthermore, the concentration of the ligand to be detected or quantitated will also influence the levels or concentration of the reactants employed for that particular test.

The concentration of the antibody employed for a particular test will be related to the range of the concentration of the ligand to be assayed.

No upper limit is attached to the amount of ligand that may be determined in accordance with the present invention because there are any techniques for dilution or attenuation of the signal detecting system that would prevent interference if excessive levels of concentrations of labeled ligand are present. The lower limit of the concentrations of the ligand which may be usefully employed for assays, is limited only be the minimum amount of chemiluminescent substance which may be detected by photodetection instruments. Since multiple chemiluminsecent molecules may be attached to a single binding partner molecule and photo detection instruments have been developed which will detect as little as $10^{-12}$ mole of chemiluminescent substances, the assay methods of the present invention have wide application.

Within certain limits, relating to the physical and chemical characteristics of the medium, to the mode of activation and to the separation process, the greater the number of chemiluminescent molecules attached to a particular ligand molecule, the greater the assay sensitivity. In such cases where multiple labels are desired, the attachment of the label may be accomplished directly by its combination with the substance to be labeled, or alternatively, several chemiluminescent molecules may first be affixed to a carrier molecule which in turn is linked to the substance.

The measurement of the quantum of light, capable of being emitted by the cyclic hydrazide (either alone, in conjugate form or when part of a reaction product), begins with the addition of an activator to an alkaline medium containing the luminescent substance to initiate and effect the light emission. A variety of activators, either alone or in combination, can be used to initiate the chemiluminescent reaction; for example, hydrogen peroxide, a peroxide producing compound (preferably microperoxidase), hypochlorite ion, ferric ion, ammonium persulfate, and the porphyrins and related compounds such as hemoglobin, cytochromes and myoglobin.

The activator, the last component of the luminescent reaction mixture to be added, is injected rapidly into the reaction medium. The ensuing light emission is recorded by instrumentation.

Kits comprising the critical reagents in a predetermined ratio can be provided to optimize the sensitivity of the assay to the concentration range of interest and to facilitate the reproducibility of results. The reagents include the labeled conjugate, the antibody which is provided in an amount at least sufficient to react with the maximum amount of the ligand expected to be determined. Besides having critical reagents in predetermined proportions, ancillary materials, for instance, buffer, stabilizers and the like may be included in the kit. The components are provided as dry powders, or concentrates which can be diluted to form the assay solutions directly and avoid the necessity of weighing the various materials.

The following examples illustrate further this invention.

EXAMPLE 1

4-[N-Ethyl-N-(4-hydroxybutyl)amino]-3-penten-2-one
(2:$R^1=C_2H_5, R^2=(CH_2)_4OH$ and $R^3=CH_3$)

4-Chloro-3-penten-2-one (2.38 g, 20 mmol), described by L. Gruber et al., Synthesis, 708, (1975), in dry THF (10 ml) was added in 5 min. to a solution of 4-(ethylamino)butanol (2.38 g, 20 mmol), described by P. N. Natarajan and S. T. Chew, Can. J. Pharm. Sci., 8, 61 (1973), and triethylamine (2.78 ml, 20 mmol), in dry THF (10 ml). After 2 h at 50°–55° C., additional amounts of 4-chloro-3-penten-2-one (1.10 g, 10 mmol) and triethylamine (1.4 ml, 10 mmol) were added. The reaction mixture was heated at 60° C. for 1 h and then cooled. The solid in the mixture was removed by filtration. The filtrate was concentrated and the oily residue was purified by chromatography (Woelm neutral $Al_2O_3$-activity II, 150 g). Elution with $CH_2Cl_2$ and $CH_3$—$COOC_2H_5$ yielded the title compound (2.4 g, 78%) as white crystals; mp 41°–41.5° C.; ir $\nu$max (KBr) 3300, 1605, 1525 and 1043 cm$^{-1}$; UV $\lambda$max ($C_2H_5OH$)

312 nm (log ε 4.38); NMR (CDCl$_3$) δ 5.09 (1H, s), 3.70 (2H, t, J=6.0 Hz), 3.29 (5H, m) 2.52 (3H, s), 2.07 (3H, s), 1.7–1.5 (4H, m) and 1.17 (3H, t, J32 7 Hz); mass spectrum m/e 199 (M+). Anal. calcd. for C$_{11}$H$_{21}$O$_2$N: C, 66.29; H, 10.62; N, 7.03; found: C, 66.02; H, 10.85; N, 6.93.

EXAMPLE 2

2-(tert-Butyldimethylsiloxy)-4-{N-[4-(tert-butyldimethylsiloxy)butyl]-N-ethylamino}-2,4-pentadiene(3: R$^1$=C$_2$H$_5$, R$^2$=(CH$_2$)$_4$OTBDMS*, R$^3$=CH$_3$ and R$^6$=TBDMS)

A solution of lithium diisopropylamide (LDA) was prepared from n-butyllithium (8.8 mmol, 2.7M in hexane) and diisopropylamine (8.8 mmol) in dry THF (9 ml) containing tetramethylethylenediamine (4.4 mmol) at 0° C. The solution of LDA was cooled to −78° C. A solution of 4-[N-ethyl-N-(4-(hydroxybutyl)amino]-3-penten-2-one (800 mg, 4 mmol), described in Example 1 in THF (5 ml) was added to the cold solution over a period of 30 min. After 2 h, a solution of tert-butyldimethylsilyl chloride (1.47 g, 9.6 mmol) in THF (5 ml) was added to the cold solution over a period of 30 min. The reaction mixture was allowed to come to room temperature (20°-22° C.) and kept that temperature for 90 min. Thereafter, the mixture was concentrated and the concentrate diluted with dry petroleum ether (bp 30°-60° C., 50 ml). The mixture was filtered under nitrogen and the filtrate concentrated. The operations of diluting, filtering and concentrating were repeated and finally the residue was stirred for 3 h under vacuum (0.2 Torr) to give the title compound (1.26 g, 2.9 mmol, 72%). An NMR spectrum of this crude product was recorded: (CDCl$_3$, N$_2$) δ 1.9 (3H, m), 0.90 (18H, m) and 0.1 (12H, m); showing the disappearance of two singlets at δ 2.52, and 2.07. This unstable product was used without further purification.
*TBDMS stands for tert-butyldimethylsilyl By following the procedure of Example 2, but replacing 4-[N-ethyl-N-(4-hydroxybutyl)amino]-3-penten-2-one with 4-(1-pyrrolidinyl)-3-penden-2-one, described by N. J. Leonard and J. A. Adamcik, J. Amer. Chem. Soc., 81, 595 (1959), 2-tertbutyldimethylsiloxy)-4-(1-pyrrolidinyl)-2,4-pentadiene, NMR (CDCl$_3$) δ 5.06 (1H, s), 3.86 (1H, s), 3.60 (1H, s), 3.06 (4H, m), 1.86 (7H, m), 0.99 (9H, s) and 0.16 (16H, m), was obtained.

By following the procedure of the preceding paragraph, but replacing tert-butyldimethylsilyl chloride with trimethylsilyl chloride, 2-(trimethylsiloxy)-4-(1-pyrrolidinyl)-2,4-pentadiene, NMR (CDCl$_3$) δ 5.00 (1H, s), 3.97 (1H, s), 3.57 (1H, s), 3.00 (4H, m), 1.78 (7H, m) and 0.13 (9H, s), was obtained.

EXAMPLE 3

5-{N-[4-(tert-butyldimethylsiloxy)butyl]-N-ethylamino}-N,3-dimethylphthalimide (4:R$^1$=C$_2$H$_5$, R$^2$=(CH$_2$)$_4$ OTBDMS and R$^3$=CH$_3$)

To a solution of N-methylmaleimide (286 mg, 2.58 mmol) in dry benzene (10 ml), the freshly prepared title compound of Example 2 (1.1 g, 2.57 mmol) in the same solvent (10 ml) was added in 30 min. at 5°-7° C. under nitrogen. After 48 h at room temperature, the reaction mixture was concentrated to dryness. The residue was mixed with 10% palladium on charcoal (100 mg) and xylene (10 ml, isomeric mixture). The mixture was refluxed for 6 h, then cooled and filtered. The filtrate was concentrated. The residue was purified by chromatography (silica gel, 100 g). Elution with CH$_2$Cl$_2$/CH$_2$COOC$_2$H$_5$ (99:1, v/v) gave the title compound (174 mg, 0.45 mmol, 17.5%) as a yellow oil; ir νmax (film) 1755, 1695, 1612, 1585, 1245, 1090 and 830 cm$^{-1}$; UV λmax (C$_2$H$_5$OH) 211, 270, 324 and 402 (log ε 4.06, 4.09, 3.51 and 3.51); NMR (CDCl$_3$) δ 6.88 (1H, d, J=1.9 Hz), 6.44 (1H, d, J=1.9 Hz; this doublet is not well defined-coupling with the 3-methyl), 3.63 (2H, t, J=5.8 Hz), 3.42 (2H, q, J=7.1 Hz), 3.35 (2H, t, J=7.6 Hz), 3.07 (3H, s), 2.55 (3H, s), 1.65–1.44 (4H, m), 1.17 (3H, t, J=5.8 Hz), 0.86 (9H, s), 0.03 (6H, s); C$_{22}$H$_{36}$O$_3$N$_2$Si requires 404.2495; found 404.2484.

By following the procedure of Example 3, but replacing the title compound of Example 2 with 2-tert-butyldimethylsiloxy)-4-(1-pyrrolidinyl)-2,4-pentadiene, N,3-dimethyl-5-(1-pyrrolidinyl)phthalamide was obtained (23.5%) as yellow needles, mp 159.5°-159.8° C., after recrystallization from CH$_2$Cl$_2$ and C$_2$H$_5$OC$_2$H$_5$; ir νmax (KBr) 1748, 1685, 1610, 1575 and 85 cm$^{-1}$; UV λmax (C$_2$H$_5$OH) 212, 268, 323 and 402 nm (log ε 4.46, 4.50, 3.93 and 3.92); NMR (CDCl$_3$) δ 6.83 (1H, d, J=2.4 Hz), 6.38 (1H, d, J=2.4 Hz); this doublet is not well defined-coupling with 3-methyl), 3.39 (4H, m; s with irradiation at δ 2.06), 3.10 (3H, s), 2.59 (3H, s) and 2.06 (4H, m; s with irradiation at δ 3.39); C$_{14}$H$_{16}$O$_2$N$_2$ requires 244.1212; found 244.1206. Anal. Calcd. C, 68.83; H, 6.60; N, 11.47; found: C, 69.19; H, 6.56; N, 11.70.

EXAMPLE 4

5-{N-[4-(tert-butyldimethylsiloxy)butyl]-N-ethylamino}-3-methylphthalic anhydride (5:R$^1$=C$_2$H$_5$, R$^2$=(CH$_2$)$_4$OTBDMS and R$^3$=CH$_3$)

To a solution of bromomaleic anhydride (684 mg, 3.87 mmol) in dry benzene (20 ml), the freshly prepared title compound of Example 2 (700 mg, 1.6 mmol) in benzene (20 ml) was added in 30 min. at 5°-7° C. under nitrogen. The dark reaction mixture was allowed to warm to room temperature and, after 15 h, the solvent was evaporated. The residue was dissolved in CH$_2$Cl$_2$. The solution was poured onto a column of silica gel (50 g). Elution with CH$_2$Cl$_2$ gave the title compound (28 mg, 0.72 mmol, 4.5%) as a yellow iol; ir νmax (film) 1827, 1765, 1617, 1580, 1250, 1090 and 830 cm$^{-1}$; UV λmax (C$_2$H$_5$OH) 214, 268, 322 and 387 nm (log ε 3.98, 3.97, 3,83 and 3,49); NMR (CDCl$_3$) δ 6.94(1H, d, J=1.9 Hz), 6.65(1H, d, J=1.9 Hz; this doublet is not well defined-coupling with the 3-methyl), 3.67(2H, t, J=5.9 Hz), 3.46(4H, m; 3.49, s and 3.42, m with irradiation at δ 1.23), 2.59(3H, s), 1.9–1.5(4H, m), 1.23(3H, t, J=7.2 Hz), 0.89(9H, s), 0.06(6H, s); C$_{21}$H$_{33}$O$_4$NSi requires 391.2179; found 391.2181. Anal. calcd: C, 64.41; H, 8.49; N, 3.57; found: C, 64.98; H, 8.45; N, 3.34.

By following the procedure of Example 4, but replacing the title compound of Example 2 with 2-(tert-butyldimethylsiloxy)-4-(1-pyrrolidinyl)-2,4-pentadiene, described in Example 2, 3-methyl-5-(1-pyrrolidinyl)-phthalic anhydride was obtained (19.5%) as yellow needles; mp 222°-225° C., ir νmax (KBr) 1823, 1753, 1620, 1578 and 865 cm$^{-1}$; UV λmax (C$_2$H$_5$OH) 212, 267, 321 and 386 nm (log ε 4.23, 4.19, 4.05 and 3,89); NMR (CDCl$_3$) δ 6.83(1H, d, J-2.2 Hz), 6.55(1H, d, J=2.2 Hz; this doublet is not well defined-coupling with the 3-methyl), 3.42(4H, m; s, with irradiation at δ 2.10), 2.59(3H, s) and 2.10(4H, m; s, with irradiation at δ 3.42); mass spectrum: m/e 231 (M+). Anal. calcd. for C$_{13}$H$_{13}$O$_3$N: C, 67.52; H, 5.66; N, 6.06; found: C, 67.65; H, 5.62; N, 6.02.

By following serially the procedures of Example 2 and 4, but replacing 4-[N-ethyl-N-(4-hydroxybutyl)amino]-3-penten-2-one with 4-(N,N-diethylamino)-3-penten-2-one, described by Leonard and Adamcik, supra, 5-(N,N-diethylamino)-3-methylphthalic anhydride was obtained (12.3%) as yellow needles; mp 128°-128.5° C., after recrystallization from $C_2H_5OC_2H_5$ and petroleum ether; ir $\nu$max (KBr) 1823, 1750, 1615, 1570 and 840 cm$^{-1}$; UV $\lambda$max ($C_2H_5OH$) 214, 268, 321 and 385 nm (log $\epsilon$ 4.33, 4.31, 4.16 and 4.00); NMR (CDCl$_3$) $\delta$ 6.94 (1H, d, J=2.2 Hz), 6.65 (1H, d of q, J=2.2 and 0.6 Hz), 3.47(4H, q, J=7.3 Hz), 2.60(3H, s), 1.24(6H, t, J=7.3 Hz); mass spectrum M/e 233 (M+); Anal. calcd. for $C_{13}H_{15}O_3N$: C, 66.93; H, 6.48; N, 6.00; found: C, 66.89; H, 6.21; N, 5.91.

EXAMPLE 5

7-{N-[4-tert-butyldimethylsiloxy)butyl]-N-ethylamino}-5-methyl-2,3-dihydro-1,4-phthalazinedione A solution of 5-{N-[4-tert-butyldimethylsiloxy)butyl]-N-ethylamino}-N,3-dimethylphthalimide (47 mg, 0.12 mmol, described in Example 3) and hydrazine hydrate (85%, 2 ml) in acetic acid (1 ml) was refluxed under nitrogen for 4 h. The reaction mixture was cooled. Collection of the precipitate yielded the title compound (32 mg, 0.079 mmol, 66%) as white crystals; mp 107°-108.5° C. after recrystallization from CH$_3$COCH$_3$ and hexanes, ir $\nu$max (KBr) 1650, 1592, 1250, 1100 and 830 cm$^{-1}$; UV $\nu$max (0.1M K$_2$CO$_3$, $c_2H_5OH$; 4:1, v/v) 224, 289 and 327 nm (log $\epsilon$ 4.24, 4.47 and 4.15); NM (CDCl$_3$) $\delta$ 7.25(1H, m), 6.86(1H, M), 3.75(2H, t, J=6.0 Hz), 3.52-3.40(4H, m), 2,87(3H, s), 1.8-1.5(4H, m), 1.24(3H, t, J=6.0 Hz), 0.9(9H, s) and 0.065(6H, s); $C_{21}H_{35}O_3N_3Si$ requires 405.2448; found 405.2444. Anal. calcd: C, 62.18; H, 8.490; N, 1035; found: C, 62.18; H, 8.69; N, 10.36.

The latter product was also prepared in the same manner from 5-{N-[4-(tert-butyldimethylsiloxy)butyl]-N-ethylamino}-3-methylphthalic anhydride of Example 4 with hydrazine hydrate.

By following the procedure of Example 5 and using the appropriate N-(lower alkyl)phthalimide from Example 3 or phthalic anhydride from Example 4, the following cyclic hydrazides were obtained: 5-methyl-7-(1-pyrrolidinyl)-2,3-dihydro-1,4-phthalazinedione (1, R$^1$ and R$^2$ together=C$_4$H$_8$ and R$^3$=CH$_3$); mp 330°-335° C. (dec), after recrystallization from CH$_3$OH and 10% NH$_4$OH in H$_2$O (v/v); ir $\nu$max (KBr) 1640, 1595, 1545 and 845 cm$^{-1}$; UV $\lambda$max (0.1M K$_2$CO$_3$) 226, 287 and 326 nm (log $\epsilon$ 4.34, 4.45 and 4.13); NMR[(CD$_3$)$_2$SO] $\delta$ 6.77(1H, s), 6.75(1H, s), 3.35(4H, m) (under H$_2$O peak visible by addition of D$_2$O; s with irradiation at $\delta$ 1.98), 2.72(3H, s), 1.98(4H, m; with irradiation at $\delta$ 3.35); mass spectrum m/e 245 (M+). Anal. calcd. for $C_{13}H_{15}O_2N_3$: C, 63.65; H, 6.16; N, 17.13; found: C, 63.78; H, 6.26; N, 16.99; was obtained from N,3-dimethyl-5-(1-pyrrolidinyl)phthalamide (63.4%) or from 3-methyl-5-(1-pyrrolidinyl)phthalic anhydride (77%). 7-(N,N-diethylamino)-5-methyl-2,3 dihydro-1,4-phthalazinedione (1; R$^1$ and R$^2$ each=C$_2$H$_5$ and R$^3$=CH$_3$); mp 290°-292° C. after recrystallization from CH$_3$OH and 10% NH$_4$OH in H$_2$O (v/v); ir $\nu$max (KBr) 1635, 1595, 1540 and 845 cm$^{-1}$; UV $\lambda$max (0.1M K$_2$CO$_3$) 227, 228 and 326 nm (log $\epsilon$ 4.17, 4.43 and 4.11); NMR [(CD$_3$)$_2$SO] $\delta$ 6.89 (2H, s), 3.44(4H, q, J=7.0 Hz), 2.72(3H, s), 1.14(6H, t, J=7.0 Hz); mass spectrum m/e 247 (M+); Anal. calcd. for $C_{13}H_1O_2N_3$: C, 63.13; H, 6.93; N, 16.99; found: C, 62.97; H, 7.20; n, 16.83; was obtained (86%) from 5-(N,N-diethylamino)-3-methylphthalic anhydride.

EXAMPLE 6

7-{N-Ethyl-N-(4-hydroxybutyl)amino}-5-methyl-2,3-dihydro-1,4-phthalazinedione(1: R$^1$=C$_2$H$_5$, R$^2$=(CH$_2$)$_4$OH and R$^3$=CH$_3$)

A mixture of 5-{N-[4-tertbutyldimethylsiloxy)butyl]-N-ethylamino}-N,3-dimethylphthalimide (56 mg, 0.144 mmol, described in Example 3) and hydrazine hydrate (85%, 1 ml) was refluxed under nitrogen for 1 h. The mixture was concentrated under vacuum and the residue was dried overnight under vacuum (0.2 Torr) over P$_2$O$_5$. The residue was dissolved in a dry THF (5 ml) solution of tetrabutylammonium fluoride (0.432 mmol, 1M in THF). The reaction mixture was stirred at room temperature for 3 h and then concentrated by evaporation of the solvent. Water (10 ml) was added to the residue. The solid in the mixture was collected by filtration to give the title compound (17 mg, 0.058 mmol, 40.6%) as light yellow crystals; mp 221°-222° C. after recrystallization from CH$_3$OH and CH$_3$COCH$_3$); ir $\nu$max (KBr) 3260, 1640, 1592, 1020 and 840 cm$^{-1}$; UV $\lambda$max (0.1M K$_2$CO$_3$) 227, 288 and 326 nm (log $\epsilon$ 4.18, 4.44 and 4.12); NMR[(CD$_3$)$_2$SO] $\delta$ 6.86(2H, s), 4.45(1H, broad, exchanges with D$_2$O), 3.40(6H, m; under H$_2$O visible by addition of D$_2$O), 2.69 (3H, s), 1.63-1.4 (4H, m) and 1.10(3H, t, J=6.7 Hz). Anal. calcd. for $C_{15}H_{21}O_3N_3$: C, 61.83; H, 7.27; N, 14.42; found: C, 61.82; H, 7.38; N, 14.42.

EXAMPLE 7

Luminescent studies

Measurements of luminescence were made on a LKB-Wallac 1251 luminometer (LKB-Produkten AB, Bromma, Sweden) using the automatic mode for injection and reading of decay portion light from the 3rd second to the 12th. Aliquots of the luminescent compound in 100 $\mu$l of phosphate buffer (0.01M phosphate-buffered saline, pH 7.4) were introduced into the cuvettes (Clinicon, polystyrene 2174-086; available from Fisher Scientific Ltd., Whitby, Ontario, Canada) and volumes were completed with 200 $\mu$l of NaOH (0.03N to 2.0N) according to the desired pH. Fixed amounts of microperoxidase (MP-11, sodium salt, Sigma Chemical Co., St-Louis, Mo., USA) (42 $\mu$l, 0.4 nM) and hydrogen peroxide (33 $\mu$l, 0.6%) were then automatically injected and the light emitted was recorded.

With known hydrazides; it is a well established fact that pH of medium used for the chemiluminescent reaction plays and important role in determining the detection limit of emitted light; see, for example, Pazzagli et al., supra. Hence, the effect of pH on the decay portion of the light produced by the present cyclic hydrazides was assessed. The results were compared with those obtained for known cyclic hydrazides. Like the known compounds, the present cyclic hydrazides (formula 1) showed a clear dependency of light yield on pH. However, the comparative data obtained in these experiments for isoluminol, two known derivatives of isoluminol namely 6-[N-(4-aminobutyl)-N-ethylamino]-2,3-dihydro-1,4-phthalazinedione and 6-[N-(6-aminohexyl)-N-ethylamino]-2,3-dihydro-1,4-phthalazinedione, previously described by Schroeder and Yeager, supra, and designated as ABEI and AHEI, respectively, and three of the present cyclic hydrazides, namely 5-methyl-7-(1-pyrrolidinyl)-2,3-dihydro-1,4-phthalazinedione (1: $R^1$ and $R^2$ together=$C_4H_8$ and $R^3$=$CH_3$);

7-(N,N-diethylamino)-5-methyl-2,3-dihydro-1,4-phthalazinedione (1: $R^1$ and $R^2$ each=$C_2H_5$ and $R^3$=$CH_3$); and 7-{N-ethyl-N-(4-hydroxybutyl)amino}-5-methyl-2,3-dihydro-1,4-phthalazinedione (1: $R^1$=$C_2H_5$, $R^2$=$(CH_2)_4OH$ and $R^3$=$CH_3$), not only showed the dependency of light yield on pH for the compounds, but also showed that the introduction of the methyl group at the C-5 position has brought about a 300–500% increase in the efficiency of the chemiluminescent process.

The following table shows the pattern of light emission with respect to time at pH 14 for isoluminol, the two known isoluminol derivatives ABEI and AHEI, and the above noted three cyclic hydrazides of formula 1.

| Compound | Percentage of light emitted between | | |
|---|---|---|---|
| | 0–2 sec. | 2–12 sec. | 12–60 sec. |
| Isoluminol | 26 | 55 | 19 |
| ABEI | 21 | 55 | 24 |
| AHEI | 22 | 56 | 22 |
| 1:$R^1$ and $R^2$ together = $C_4H_8$ and $R^3$ = $CH_3$ | 25 | 60 | 15 |
| 1:$R^1$ and $R^2$ each = $C_2H_5$ and $R^3$ = $CH_3$ | 25 | 57 | 18 |
| 1:$R^1$ = $C_2H_5$, $R^2$ = $(CH_2)_4OH$ and $R^3$ = $CH_3$ | 22 | 56 | 22 |

The similarity of the time-scale patterns of light emission for both the former and present compounds strongly suggests that greater efficiency of the luminescent process for the present cyclic hydrazides over the known ones is not due to a change in the kinetics of the luminescent reaction that the compounds undergo, because for both the present and former compounds approximately 55% of the light emission occurs between the 3rd and 12th second at pH 14 during the reaction.

EXAMPLE 8

Immunologically active conjugate of a monoclonal antibody to the α-subunit of human chorionic gonadotropin and 7-{N-ethylamino-N-(4-hydroxybutyl)amino}-5-methyl-2,3-dihydro-1,4-phthalazinedione (i.3. title compound of Example 6).

(a) Hemisuccinate of the title compound of Example 6.

A solution of the title compound of Example 6 (5 mg, 0.017 mmol) and succinic anhydride (2.5 mg, 0.025 mmol) in dry pyridine (0.1 ml) was stirred at room temperature for 4 days. The reaction mixture was subjected to thin layer chromatography on plates precoated with silica gel 60F254 (Merck, no. 5554). The solvent system used was $CH_2Cl_2$, $CH_3OH$, $CH_3COOH$ (95:5:1). After two migrations, the most polar band was extracted with $CH_2Cl_2$, $CH_3OH$, $CH_3COOC_2H_5$ (1:1:1) to give the hemisuccinate (6 mg) as a white powder ir $\nu$max (KBr) 1735, 1655, 1600 cm$^{-1}$.

(b) Coupling of the hemisuccinate with the antibody

A solution of the hemisuccinate (1 mg, 3 μmol), hydroxysuccinimide (500 μg, 4.3 μmol) and dicyclohexylcarbodiimide (618 μg, 3 pmol) in dry dimethylformamide (100 μl) was stirred at room temperature for 16 h. An aliquot from the preceding solution (15 μl containing 0.45 μmole of the activated hemisuccinate) was added at 0° C. to a cold solution of a monoclonal anti α hCG (H25-245-14-10), 250 μg, available from Bio-Mega Diagnostic Inc., Montreal, in 500 μl of phosphate buffer (50 mM, pH8.5). The mixture was stirred at 0° C. for 2 h and then kept at 4° C. for 16 h. The conjugate was isolated by filtration of the mixture through a G-25 Sephadex column (1×7 cm) using phosphate-saline buffer with 0.25% bovine serum albumin (pH 7.5) as eluant.

The activity of the conjugate was demonstrated by immunometric assay.

What is claimed is:

1. A cyclic hydrazide of formula 1

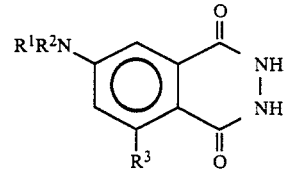

wherein $R^1$ and $R^2$ together with the nitrogen to which they are attached represent a 1-pyrrolidinyl, 1-piperidinyl or 1-azepinyl; or $R^1$ is lower alkyl and $R^2$ is lower alkyl or a substituted alkyl of the formula $CHR^4CHR^5$-ALK-X wherein each of $R^4$ and $R^5$ is hydrogen or methyl, ALK is a divalent alkylene having 1 or 2 carbon atoms, or 3 to 5 carbon atoms in a straight chain, with optional substitution of a methyl on one or more of the carbon atoms, and X is halo, hydroxy, carboxy or amino; and $R^3$ is lower alkyl.

2. A cyclic hydrazide of claim 1 wherein $R^1$ and $R^2$ together with the nitrogen to which they are attached represent a 1-pyrrolidinyl or 1-piperidinyl, and $R^3$ is methyl, ethyl, propyl or butyl.

3. A cyclic hydrazide of claim 1 wherein each of $R^1$, $R^2$ and $R^3$ is methyl, ethyl, propyl or butyl.

4. A cyclic hydrazide of formula 1

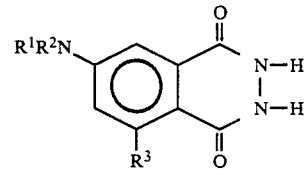

wherein each of $R^1$ and $R^3$ is lower alkyl and $R^2$ is $CH_2$—$CH_2$—ALK-X wherein ALK is a divalent alkylene having 1 or 2 carbon atoms, or 3 to 6 carbon atoms in a straight chain, and X is hydroxy, carboxy or amino.

5. A cyclic hydrazide of claim 4 wherein each of $R^1$ and $R^3$ is methyl or ethyl and $R^2$ is $(CH_2)_mX$ wherein m is an integer from 3 to 8 and X is hydroxy, carboxy or amino.

6. The cyclic hydrazide of claim 2 which is 5-methyl-7-(1-pyrrolidinyl)-2,3-dihydro-1,4-phthalazinedione.

7. The cyclic hydrazide of claim 3 which is 7-(N,N-diethylamino)-5-methyl-2,3-dihydro-1,4-phthalazinedione.

8. The cyclic hydrazide of claim 5 which is 7{N-ethyl-N-(4-hydroxybutyl)amino}-5-methyl-2,3-dihydro-1,4-phthalazinedione.

9. N,3-Dimethyl-5-(1-pyrrolidinyl)-phthalimide.

10. 5-{N-[4-(tert-Butyldimethylsilyloxy)butyl]-N-ethylamino}-N,3-dimethylphthalimide.

11. 3-Methyl-5-(1-pyrrolidinyl)phthalic anhydride.

12. 5-(N,N-Diethylamino)-3-methylphthalic anhydride.

13. 5-{N-[4-(tert-Butyldimethylsiloxy)butyl]-N-ethylamino}-3-methylphthalic anhydride.

14. A luminescent composition for reaction with an activator to produce chemiluminescent light which comprises a cyclic hydrazide of formula 1 as claimed in claim 1 and an aqueous alkaline medium for the cyclic hydrazide.

15. A process for producing a luminescent light which comprises reacting a cyclic hydrazide of formula 1, as claimed in claim 1, with an activator capable of effecting a chemiluminescent reaction.

* * * * *